United States Patent
Parkes (10) Patent No.: US 9,849,256 B2
(45) Date of Patent: Dec. 26, 2017

(54) MEDICAMENT DELIVERY DEVICES

(71) Applicant: INNOVATA BIOMED LIMITED, Edinburgh (GB)

(72) Inventor: Philip Carl Parkes, Edinburgh (GB)

(73) Assignee: Innovata Biomed Limited, Edinburgh (GB)

(*) Notice: Subject to any disclaimer, the term of this patent is extended or adjusted under 35 U.S.C. 154(b) by 656 days.

(21) Appl. No.: 14/374,306

(22) PCT Filed: Jan. 17, 2013

(86) PCT No.: PCT/GB2013/050101
§ 371 (c)(1),
(2) Date: Jul. 24, 2014

(87) PCT Pub. No.: WO2013/110927
PCT Pub. Date: Aug. 1, 2013

(65) Prior Publication Data
US 2015/0040901 A1 Feb. 12, 2015

(30) Foreign Application Priority Data
Jan. 26, 2012 (GB) .................................. 1201272.0

(51) Int. Cl.
*A61M 15/00* (2006.01)
*G06M 1/24* (2006.01)
*G06M 3/02* (2006.01)

(52) U.S. Cl.
CPC ........ *A61M 15/0081* (2014.02); *A61M 15/00* (2013.01); *A61M 15/0003* (2014.02);
(Continued)

(58) Field of Classification Search
CPC .............................................. A61M 15/0081
See application file for complete search history.

(56) References Cited

U.S. PATENT DOCUMENTS

| 4,074,827 A * | 2/1978 | Labe, III | ................ B65D 51/28 |
| | | | 206/217 |
| 4,725,461 A * | 2/1988 | Masui | ................ D04D 7/105 |
| | | | 428/101 |

(Continued)

FOREIGN PATENT DOCUMENTS

| EP | 0539469 B1 | 4/1995 |
| EP | 1233805 B1 * | 3/2004 | ........ A61M 15/0065 |

(Continued)

OTHER PUBLICATIONS

International Search Report in connection with International Application No. PCT/GB2013/050101 dated Apr. 29, 2013.

(Continued)

*Primary Examiner* — (Jackie) Tan Uyen T Ho
*Assistant Examiner* — Joseph D Boecker
(74) *Attorney, Agent, or Firm* — Davidson, Davidson & Kappel, LLC (57) ABSTRACT

A medicament delivery device (1) comprises an actuation mechanism by successive operation of which a predetermined number of unit doses of medicament can be dispensed. The device includes a locking mechanism for preventing further operation of the actuation mechanism after dispensing of said predetermined number of unit doses. The locking mechanism comprises a resilient member (51), a formation (18) with which the resilient member (51) is engageable to disable operation of the actuation mechanism, and a barrier member (20) that prevents engagement of the resilient member (51) and the formation (18) until said predetermined number of unit doses has been dispensed. The device (1) may be a dry powder inhaler.

20 Claims, 7 Drawing Sheets

(52) U.S. Cl.
CPC ...... *A61M 15/007* (2014.02); *A61M 15/0065* (2013.01); *A61M 15/0078* (2014.02); *G06M 1/246* (2013.01); *G06M 3/02* (2013.01); *A61M 2202/0007* (2013.01); *A61M 2202/064* (2013.01); *A61M 2205/0216* (2013.01); *A61M 2205/273* (2013.01)

(56) References Cited

U.S. PATENT DOCUMENTS

| | | | | |
|---|---|---|---|---|
| 5,025,947 | A | * | 6/1991 | Leone .................... A47G 21/18 220/229 |
| 5,263,475 | A | | 11/1993 | Altermatt et al. |
| 5,347,998 | A | * | 9/1994 | Hodson ............. A61M 15/0091 128/200.23 |
| 6,422,236 | B1 | * | 7/2002 | Nilsson ............. A61M 15/0045 128/203.15 |
| 2004/0094147 | A1 | | 5/2004 | Schyra et al. |
| 2014/0150778 | A1 | * | 6/2014 | Malhotra .......... A61M 15/0075 128/200.23 |

FOREIGN PATENT DOCUMENTS

| | | |
|---|---|---|
| EP | 1616592 A1 | 1/2006 |
| EP | 1992376 | 11/2008 |
| EP | 1992379 A1 | 11/2008 |
| JP | 2011024705 | 2/2011 |
| WO | WO01/03851 | 1/2001 |
| WO | WO 2005/102430 A1 | 11/2005 |
| WO | WO 2008/077623 A1 | 7/2008 |
| WO | WO2008/079350 | 7/2008 |
| WO | WO 2008/086413 A2 | 7/2008 |
| WO | WO 2009/087404 A1 | 7/2009 |

OTHER PUBLICATIONS

International Preliminary Report on Patentability in connection with International Application No. PCT/GB2013/050101.

* cited by examiner

MEDICAMENT DELIVERY DEVICES

This application is a national phase application under 35 U.S.C. §371 of International Application No. PCT/GB2013/050101, filed Jan. 17, 2013, which claims priority to GB 1201272.0, filed on Jan. 26, 2012, the disclosures of which are all hereby incorporated by reference herein.

FIELD OF THE INVENTION

This invention relates to improvements to medicament delivery devices, and in particular to mechanisms by which operation of such a device is disabled after a predetermined number of actuations of the device. The mechanisms are of particular utility in relation to devices for the administration of medicaments by inhalation, especially in dry powder inhalers.

BACKGROUND

The administration of medicaments by inhalation is well-known. A wide variety of medicaments are now administered by that route, for the treatment of a range of respiratory disorders.

The most common form in which such medicaments are formulated for administration by inhalation is as a powder. In the past, many such compositions were formulated as pressurised aerosols, in which the powder medicament was suspended in a liquefied propellant. Due to the adverse environmental effects of the propellants conventionally used, however, there is now increased interest in the use of so-called dry powder inhalers (DPIs). In a DPI, a unit dose of medicament powder, either packaged as such or metered from a bulk reservoir of medicament, is presented to an airway and is then entrained in an airflow passing through the airway. The airflow is most commonly generated by the patient's act of inhalation.

DPIs, such as the CLICKHALER® inhaler produced by Innovata. Biomed in the UK and described in EP0539469B, preferably include a dose counter mechanism for providing an indication of the number of doses that have been administered to a patient and/or the number of doses that remain in the inhaler. Conventional dose counter mechanisms for use with DPIs comprise a ratchet mechanism with indicia being carried by the ratchet wheel.

WO2005/102430 discloses a dose counter mechanism for a DPI that comprises a tape carrying numbers that are visible at a tape display area. Actuation of the DPI causes the tape to index and a different number to be displayed at the tape display area, thereby giving a visual indication of the number of doses that have been dispensed.

Whilst the dose counter mechanism disclosed in WO2005/5102430 is beneficial, further improvement of it would be advantageous. In particular, it would be desirable for the dose counter mechanism to not only indicate to a user of the DPI device the number of doses that have been dispensed (or, alternatively, the number of doses that remain to be dispensed), but also to prevent continued actuation of the device after the last intended dose has been dispensed. Otherwise, a patient may continue to use the device, believing that further doses of medicament are being dispensed when in fact the device is exhausted.

SUMMARY OF THE INVENTION

There has now been devised an improvement to medicament delivery devices that addresses the above-mentioned need, and/or which overcomes or substantially mitigates the above-mentioned and/or other disadvantages associated with the prior art.

According to a first aspect of the invention, there is provided a medicament delivery device comprising an actuation mechanism by successive operation of which a predetermined number of unit doses of medicament can be dispensed, the device including a locking mechanism for preventing further operation of the actuation mechanism after dispensing of said predetermined number of unit doses, characterised in that said locking mechanism comprises a resilient member, a formation with which the resilient member is engageable to disable operation of the actuation mechanism, and a barrier member that prevents engagement of the resilient member and the formation until said predetermined number of unit doses has been dispensed.

The medicament delivery device is advantageous primarily in that engagement of the resilient member with the formation prevents further actuation of the device, and so eliminates the possibility of a patient continuing to use the device after the intended number of doses has been dispensed. The resilient member may be biased into engagement with the formation, such engagement being prevented by the barrier member until that number of doses has been dispensed.

The medicament delivery device may be an inhaler, and in particular may be a DPI. However, the invention may find utility in other forms of medicament delivery device, eg nasal spray devices and the like. In general, the device may have any form in which a predetermined number of unit doses are dispensed. In some embodiments, the device will include a reservoir in which a bulk quantity of medicament is held, the unit doses being dispensed as aliquots from that bulk quantity. In other embodiments, the device may be loaded with a plurality of discrete unit doses.

The device may be used to dispense unit doses of a single medicament. Alternatively, the device may be used to dispense unit doses of a formulation containing two or more medicaments. In a further alternative, the device may be used to dispense unit doses of two or more medicaments from separate reservoirs within the device, those unit doses then being administered to the patient simultaneously.

In many embodiments of the device according to the invention, operation of the device is brought about by means of a push-button or the like, which acts upon a dispensing actuator that undergoes a reciprocating motion. By "reciprocating motion" is meant displacement in one direction along a path and then return in the opposite direction along the same path. The path may be linear or have some other suitable form, eg the path may be arcuate or radiussed.

In some embodiments, operation of the device not only causes dispensing of a unit dose of medicament (or medicaments), but also operates a dose counting mechanism that provides to the user of the device an indication of the number of doses that have been dispensed (or alternatively the number of doses that remain counter actuator. The dispensing actuator and the dose counter actuator may be integrally formed as a single component.

The resilient member may be an elongate arm that is displaced along an axis parallel to the axis of reciprocating movement of the dose counter actuator. The arm may have a projection that in the course of that reciprocating action is brought into registration with the formation, which may be a recess or opening in an adjacent component of the device. The arm is preferably formed integrally with the dispensing actuator.

The barrier member may be part of the dose counting mechanism, the barrier member being interposed between the resilient member and the formation until the last of the predetermined number of unit doses has been dispensed. Operation of the device to dispense the last of the predetermined doses may have the effect of removing the barrier member from between the resilient member and the formation, thereby permitting the resilient member to engage the formation and preventing further operation of the device.

In some embodiments, the device incorporates a dose counting mechanism in which indicia showing the number of doses dispensed or remaining are carried on an element that is displaced upon each actuation. That element may constitute the barrier element. The indicia may be numbers or may be some other visual indication of the number of doses dispensed or remaining, eg a graduation in pattern or colour.

In currently preferred embodiments of the invention, the dose counting mechanism comprises a tape that carries indicia showing the number of doses dispensed or remaining. The tape is wound on a take-up spool and is indexed upon each actuation of the device. The tape may pass between the resilient member and the formation during at least part of the actuation process, and may thereby prevent engagement of the resilient member with the formation. The tape may thus constitute the barrier member.

The tape may be configured such that once the predetermined number of unit doses has been dispensed it ceases to act as a barrier between the resilient member and the formation. For instance, the tape may have a length such that an end of the tape clears the area between the resilient member and the formation once the last of the predetermined number of doses has been dispensed. More preferably, however, the tape is formed with an opening, a puncture or an area of weakness that is brought into registration with the formation upon dispensing of the last of the predetermined doses, thereby removing the barrier between the formation and the resilient member and allowing the formation and the resilient member to engage. The tape may, for instance, have an opening (square, rectangular, circular, elliptical or any other suitable shape) formed in it.

Alternatively, the tape may have one or more slits formed in it, such that the resilient member is able to penetrate the tape in the region of the slit(s). In a currently particularly preferred arrangement, the tape is formed with an axial slit that is intersected by one or more transverse slits.

Engagement of the resilient member with the formation preferably prevents further movement of the dispensing actuator. In some preferred embodiments, the resilient member engages the formation when the dispensing actuator is in its depressed position. As the dispensing actuator will normally be biased to the opposite extent of its travel, this provides an immediate visual indication that the device has been exhausted (ie that the predetermined number of doses has been dispensed).

Thus, according to another aspect of the invention, there is provided a medicament delivery device comprising a dispensing actuator by successive operation of which a predetermined number of unit doses of medicament can be dispensed, the device including a locking mechanism for preventing further operation of the dispensing actuator after dispensing of said predetermined number of unit doses, and the dispensing actuator being capable of reciprocating motion between a rest position and a depressed position, the dispensing actuator being biased to the rest position and after dispensing of said predetermined number of unit doses being locked in the depressed condition.

The locking mechanism may form part of a dose counting mechanism of the kind disclosed in WO2005/102430. Such a mechanism comprises a tape carrying numbers that are visible at a tape display area, the tape being held in a tape dispenser housing with a tape collector spool. Actuation of the device causes the tape to index and a different number to be displayed at the tape display area, thereby giving a visual indication of the number of doses that have been dispensed (or the number that are remaining).

The tape may be formed of a plastics material. The indicia are preferably printed on a surface of the tape, and preferably take the form of a series of numbers that indicate either the number of doses administered or the number of doses remaining within the medicament delivery device.

The tape dispenser housing preferably comprises an enclosure within which a roll of the tape is housed, and an opening through which the tape exits the tape dispenser housing. Most preferably, the tape dispenser housing has an opening that is sufficiently large for the roll of tape to be introduced into the tape dispenser housing, but is configured so as to retain the roll of tape within the tape dispenser housing, during use. In preferred embodiments, the tape dispenser housing comprises an enclosing wall having a generally C-shaped cross-section, and end flanges that prevent any lateral movement of the roll of tape.

It is particularly preferred that the tape that is held in the tape dispenser housing is formed into a simple roll, without being wound on a bobbin or the like.

The tape display area preferably has a smooth and generally flat surface that the tape overlies in use, at least one of the indicia provided on the part of the tape overlying the tape display area preferably being visible to a user. The tape may be indicia. In this case, the tape display area is preferably coloured distinctly relative to the colour of the indicia.

The collector spool is preferably rotatably mounted within a collector spool housing. The dispenser housing, the collector spool housing, and the tape display area are preferably formed as a single component, preferably by injection moulding in a plastics material.

A retaining clip is preferably also provided to ensure that the tape is sufficiently taut for the indicia to be readily visible and for the movement of the tape in use to be precise enough to ensure accurate counting of the doses. The retaining clip may also act to ensure that the tape lies flat against the tape display area during use, and to assist in retaining the roll of tape within the tape dispenser housing.

The dose counter mechanism preferably includes a dose counter actuator that acts to rotate the collector spool appropriately during use. In particular, the dose counter actuator preferably rotates the collector spool by a predetermined degree each time a dose of medicament is dispensed from the medicament delivery device. Most preferably, this rotation of the collector spool by a pre-determined degree each time a dose of medicament is dispensed from the medicament delivery device causes the indicia visible to the user to change, preferably to an adjacent indicia provided on the tape. The dose counter actuator is therefore preferably operably linked to the dispensing actuator. Most preferably, the dose counter actuator and the dispensing actuator are integral with each other.

Where the dispensing actuator is displaced along a linear path and then returned to its rest position each time a dose of medicament is dispensed, the dose counter actuator is also preferably displaced along a linear path and then returned to its rest position each time a dose of medicament is dispensed. The dose counter actuator is therefore preferably adapted to rotate the collector spool by a predetermined degree on being displaced along a linear path and then returned to its rest position.

In some embodiments, the collector spool comprises an end plate having a plurality of projections that are engageable by the dose counter actuator, during use, to cause rotation of the collector spool. Preferably, the projections are spaced equi-angularly about a peripheral part of the end plate.

The dose counter actuator preferably comprises first and second actuator arms, the first actuator arm engaging the collector spool when the dose counter actuator is displaced from its rest position, and the second actuator arm engaging the collector spool on the return stroke of the dose counter actuator to its rest position. Most preferably, the second actuator arm is engaged with a projection when the dose counter actuator is in its rest position, and the first actuator arm engages a projection upon displacement of the dose counter actuator from its rest position, which then causes the first actuator arm to exert a force on the projection with which it is engaged so as to rotate the collector spool. The second actuator arm engages a projection on the return stroke of the dose counter actuator. The first and second actuator arms thus engage projections on opposite sides of the axis of rotation of the collector spool. In this way, the collector spool is rotated by the movement of the dose counter actuator and rotation of the collector spool in the reverse direction is prevented.

The medicament delivery device is preferably an inhaler, and more preferably a DPI, such as the CLICKHALER® inhaler produced by Innovata Biomed in the UK and described in EP0539469B or the combination therapy DPI described in WO01/39823.

A variety of medicaments may be administered using the inhaler of the invention. Such medicaments are generally suitable for the treatment of asthma, COPD and respiratory infections. Such medicaments include, but are not limited to $\beta_2$-agonists, eg fenoterol, formoterol, pirbuterol, reproterol, rimiterol, salbutamol, salmeterol and terbutaline; non-selective beta-stimulants such as isoprenaline; xanthine bronchodilators, eg theophylline, aminophylline and choline theophyllinate; anticholinergics, eg ipratropium bromide, oxitropium and tiotropium; mast cell stabilisers, eg sodium cromoglycate and ketotifen; bronchial anti-inflammatory agents, eg nedocromil sodium; and steroids, eg beclomethasone, fluticasone, budesonide, flunisolide, triamcinolone, mometasone and ciclesonide; and/or salts or derivatives thereof.

Specific combinations of medicaments which may be mentioned include combinations of steroids and $\beta_2$-agonists. Examples of such combinations are beclomethasone dipropionate and formoterol; beclomethasone dipropionate and salmeterol; fluticasone and formoterol; fluticasone and salmeterol; budesonide and formoterol; budesonide and salmeterol; flunisolide and formoterol; flunisolide and salmeterol; ciclesonide and salmeterol; ciclesonide and formoterol; mometasone and salmeterol; and mometasone and formoterol.

Further medicaments which may be mentioned include systemically active materials, such as proteinaceous compounds and/or macromolecules, for example hormones and mediators, such as insulin, human growth hormone, leuprolide and alpha interferon, growth factors, anticoagulants, immunomodulators, cytokines and nucleic acids.

BRIEF DESCRIPTION OF THE DRAWINGS

One embodiment of the invention will now be described in greater detail, by way of illustration only, with reference to the accompanying drawings, in which.

DETAILED DESCRIPTION

Figure 1:
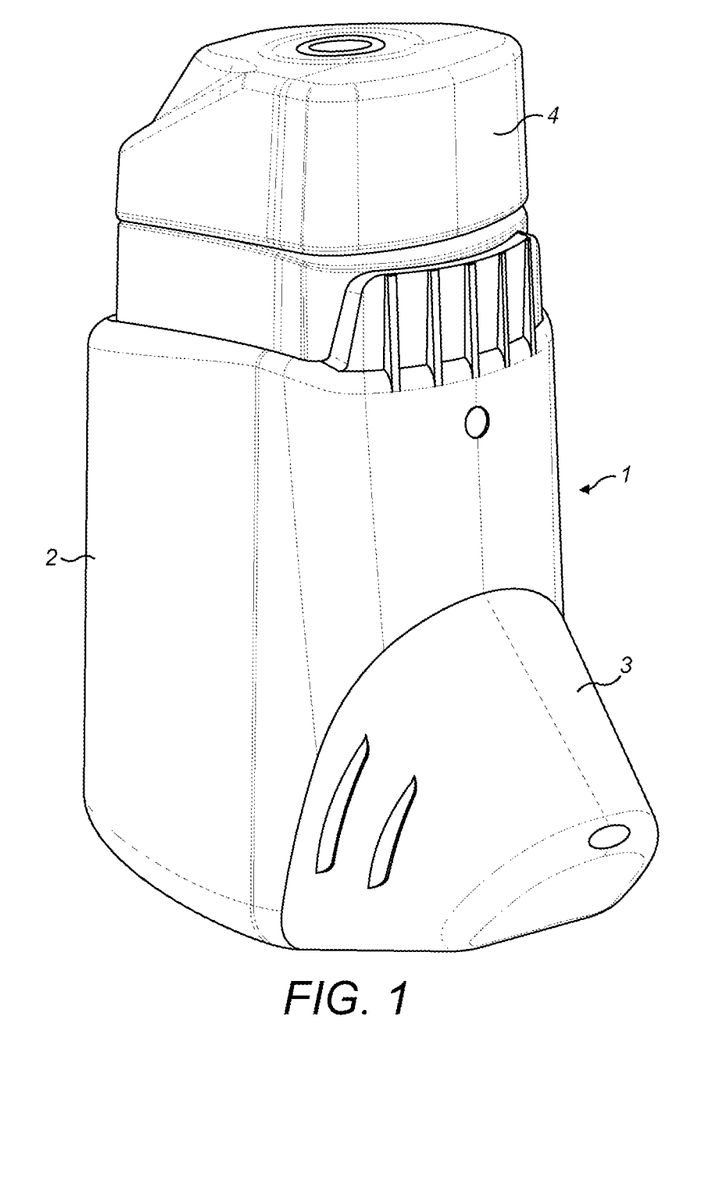
FIG. 1 is a perspective view of a dry powder inhaler device according to the invention.

Referring first to FIG. 1, a dry powder inhaler is generally designated 1 and comprises a body 2 with an integral mouthpiece that is covered by a removable cap 3. The upper (as viewed in FIG. 1) part of the inhaler 1 comprises a depressible push-button 4. The inhaler 1 includes a dose dispensing mechanism (not visible) that is broadly as described in EP1233805B. The inhaler 1 further comprises a dose counter mechanism that incorporates a device locking mechanism according to the invention, which prevents further actuation of the device once a predetermined number of actuations of the device have occurred and which is described below.

Figure 2:
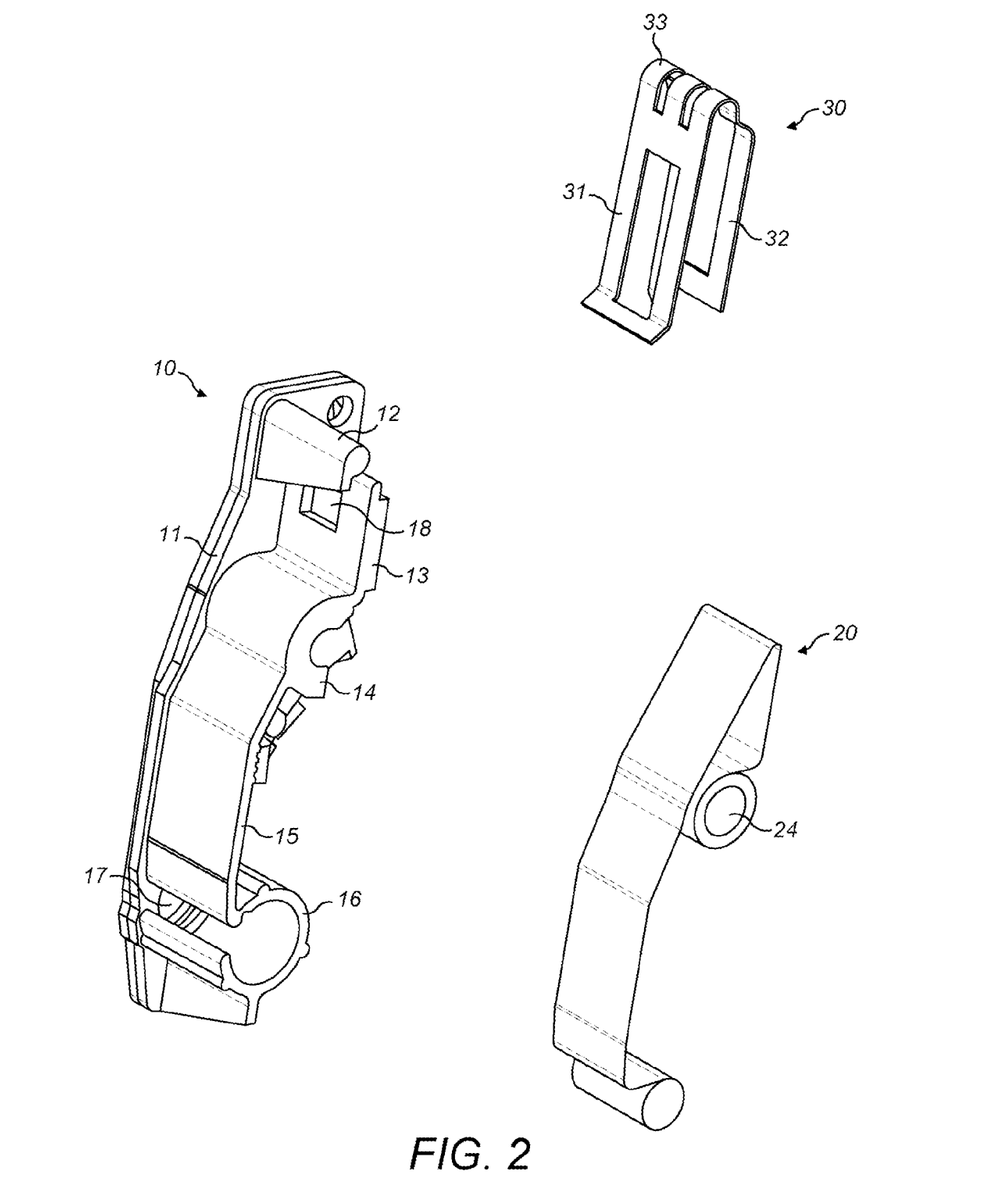
FIG. 2 shows a tape housing, a tape, and a retaining clip, which together form part of a dose counter mechanism that forms part of the device of FIG. 1 and incorporates a device locking mechanism according to the invention.
Figure 3:
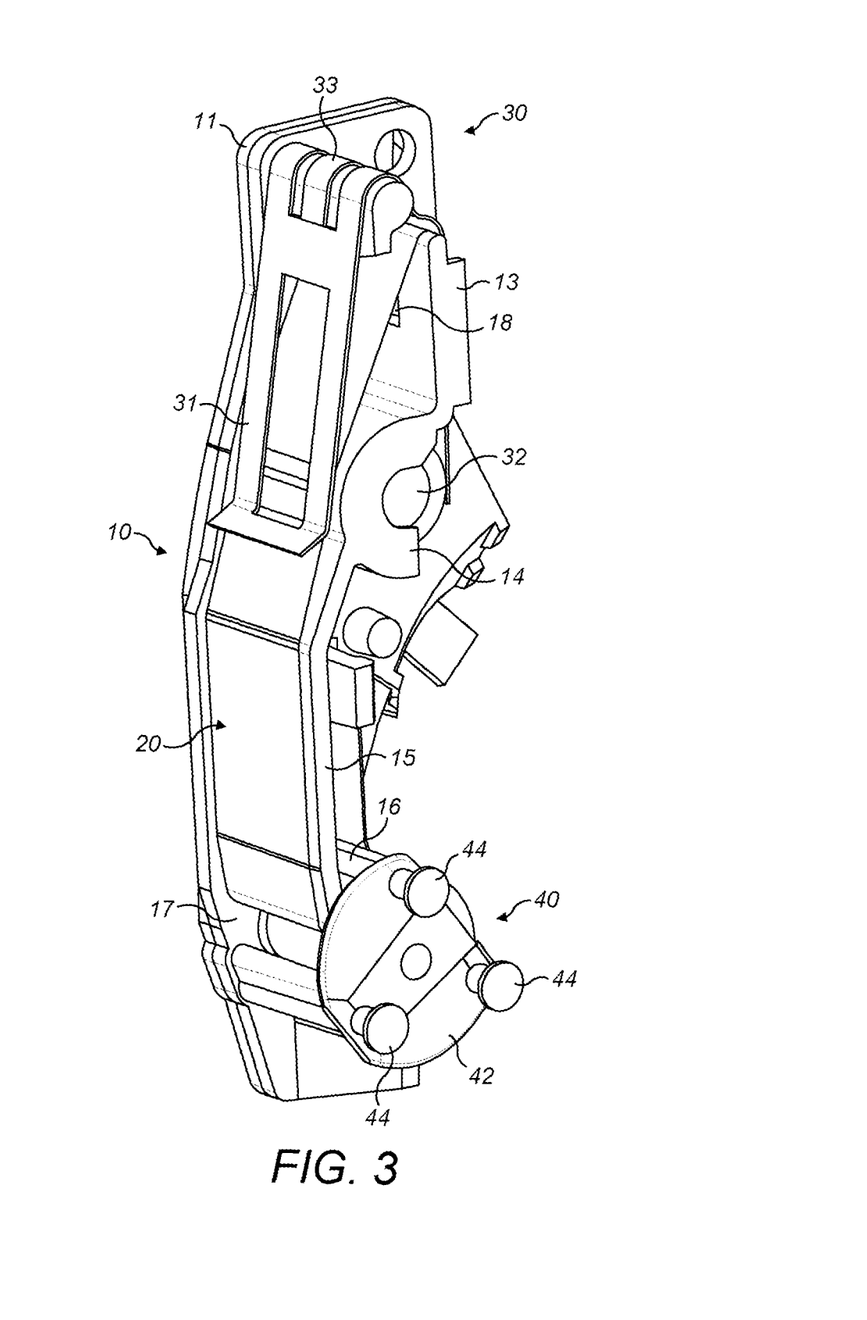
FIG. 3 is a perspective view of the tape housing, tape, and retaining clip of the dose counter mechanism, as well as a collector spool that also forms part of the dose counter mechanism, in an assembled configuration.
Figure 4:
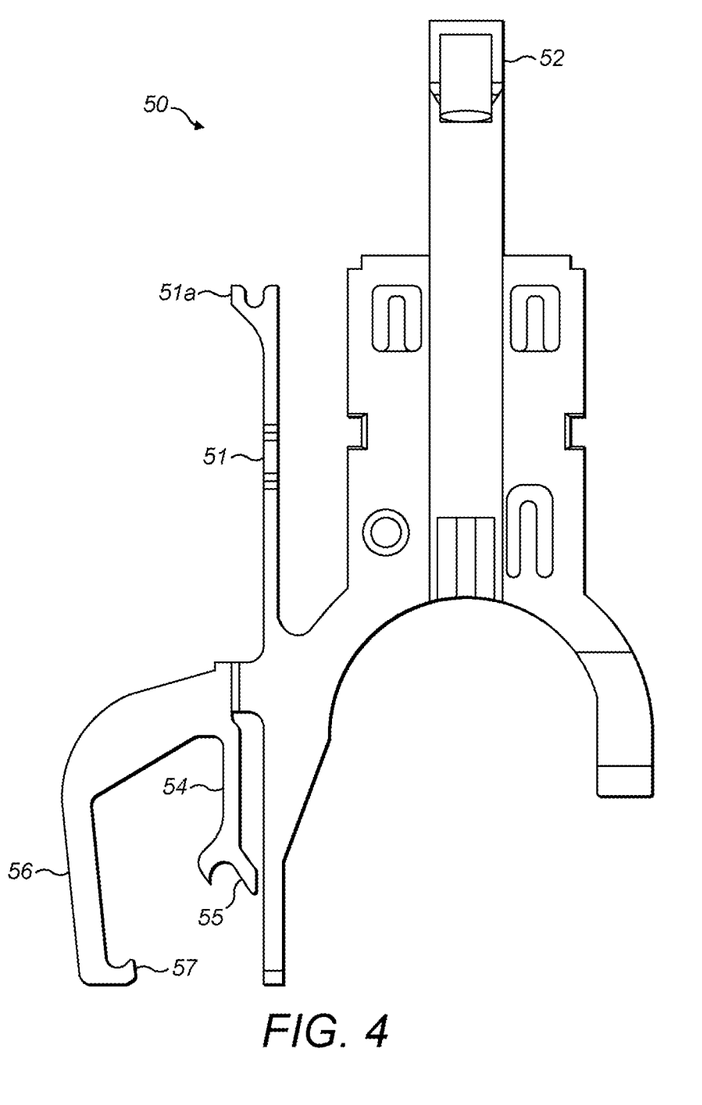
FIG. 4 is a side view of a dose counter actuator that forms part of the dose counter mechanism.

Referring now to FIGS. 2 to 4, the dose counter mechanism comprises a tape housing 10, a tape 20, a retaining clip 30, a collector spool 40, and an actuator 50 that combines the functions of a dispensing actuator and a dose counter actuator. The actuator 50 includes an integral locking arm 51, the operation of which is described in detail below.

The tape housing 10 is injection moulded in plastics material as a single component, and is shown in FIG. 2. The tape housing 10 comprises a side wall 11 that is adapted to be attached to a relevant part of the dry powder inhaler 1. Extending from one side of the side wall 11 is a first member 12 having a generally radiussed upper surface (as viewed in FIG. 2), and a second member having a rear wall 13, a dispenser housing 14, a tape display plate 15, and a collector spool housing 16. A small gap exists between the underside of the first member 12 and the upper edge of the rear wall 13.

A generally square opening 18 is formed in the rear wall 13 of the tape housing 10.

The rear wall 13 is orientated substantially along the longitudinal axis of the tape housing 10, and is situated slightly below and rearward (as viewed in FIG. 2) of the first member 12. The dispenser housing 14 extends from the lower end of the rear wall 13, and comprises a front enclosing wall of C-shaped cross-section and a C-shaped end flange. An opening is therefore defined at the rear of the dispenser housing 14. In an assembled configuration, the dispenser housing 14 holds a roll of tape 20, and the end flange prevents any lateral movement of the roll of tape 20, during use.

A tape display plate 15 extends from a lower part of the dispenser housing 14 to the collector spool housing 16 at the lower end of the tape housing 10 (as viewed in FIG. 2). The front surface of the tape display plate 15 is smooth and generally flat. The smooth and generally flat nature of the front surface of the tape display plate 15 enables the tape 20 to be presented to a user in an easily readable configuration.

The collector spool housing 16 is cylindrical in form with one end extending from the side wall 11 of the tape housing 10, and the other end being open. A slot 17 is provided in the wall of the collector spool housing 16 through which the tape 20 enters before being wound on the collector spool 40 (part of which is visible in FIG. 3). The surface defining the upper edge of the slot 17 is rounded.

The tape 20 is shown in FIG. 2 in a configuration that the tape 20 adopts when assembled within the dose counter mechanism. The tape 20 is a transparent plastics film with a series of numbers (not shown), from zero to a number that indicates the number of doses contained within the fully charged dry powder inhaler 1, printed on a surface of the tape 20. The tape 20 is in the form of a roll 24 with the numbers printed in a colour that is clearly visible against the background formed by the tape display plate 15. The tape is simply formed into the roll 24, which is then inserted into the dispenser housing 14.

The retaining clip 30 is formed from a resilient metal, such as stainless steel, and has the form shown in FIG. 2. In particular, the retaining clip 30 comprises a front retainer 31, a rear retainer 32, and a connecting portion 33. The front and rear retainers 31, 32 each include a pair of parallel arms that are planar in form and adapted to overlie the outer surface of the tape 20 in the assembled dose counter mechanism. The lower ends (as viewed in FIG. 2) of the arms of the front and rear retainers 31, 32 are outwardly turned. The connecting portion 33 comprises three parallel members. The outer two members of the connecting portion 33 connect the front and rear retainers 31, 32, and are shaped to conform to the radiussed upper surface of the first member 12. The central member of the connecting portion 33 has the form of a clip that engages the first member 12 in the assembled configuration of the dose counter mechanism.

FIG. 3 shows the tape housing 10, tape 20, retaining clip 30, and collector spool 40 in an assembled configuration. The roll of tape 20 is held within the dispenser housing 14 by the rear retainer 32 of the retaining clip 30. The tape 20 extends from the dispenser housing 14, along the rear surface of the rear wall 13, through the gap between the first member 12 and the upper edge of the rear wall 13, along the front surface of the tape display plate 15, through the slot 17, and into the collector spool housing 16. The retaining clip 30 is engaged with the first member 12 so as to maintain the tape 20 in a relatively taut state, to urge the tape 20 against the front surface of the tape display plate 15, as well as preventing displacement of the roll of tape from the dispenser housing 14 and providing uniform tension in the tape 20 to ensure accurate counting of the doses. The tape 20, in passing along the rear surface of the rear wall 13, occludes the opening 18 in the rear wall 13.

The collector spool 40 comprises an end plate 42 that is in abutment with the open end of the collector spool housing 16, and a cylindrical shaft (not visible in FIG. 3) housed within the collector spool body 16, the end of which engages in an opening in the side wall 11 of the tape housing 10 such that the collector spool 40 can rotate. The tape 20 enters the collector spool housing 16 through the slot 17, and is guided by the surface of the collector spool housing 16 that defines the upper edge of the slot 17 onto the collector spool 40. The end of the tape 20 is fixed to the collector spool 40 such that rotation of the collector spool 40 in a clockwise direction (as viewed in FIGS. 2 and 3) winds the tape onto the cylindrical body of the connector spool 40.

The end plate 42 has the form of a D-shaped disc, with three pegs 44 provided on the outwardly-facing surface of the end plate 42. The three pegs 44 are spaced equi-angularly about a peripheral part of the outwardly-facing surface of the end plate 42, and each peg 44 comprises a cylindrical neck and an enlarged head.

In the fully charged inhaler 1, the dose counter mechanism is assembled such that the majority of the tape 20 is held in the dispenser housing 14 in the form of a roll 24. As described above, the tape 20 extends along the front surface of the tape display plate 15, and the end of the tape 20 is fixed to the collector spool 40. In this configuration, the printed number that indicates the number of doses contained within the fully charged dry powder inhaler is located over a viewing part of the tape display plate 15. The inhaler 1 has a transparent window (not visible in FIG. 1) that overlies the viewing part of the tape display plate 15, such that this printed number is visible to the user.

To dispense a dose of medicament from the inhaler 1, the user depresses and releases the push-button 4, which is connected to the dose counter actuator 50 of FIG. 4. The actuator 50 is spring-loaded so that it (and the push-button 4) returns to its rest configuration once released by the user.

Each depression and release of the actuator 50 causes the collector spool 40 to be rotated through 120°, thereby causing a pre-determined length of the tape 20 to be wound onto the collector spool 40. This, in turn, causes the tape 20 to be advanced along the tape display plate 15, such that the next printed number in the series is located over a viewing part of the tape display plate 15 and hence is visible through the transparent window of the inhaler 1.

This action is achieved by virtue of the form of the actuator 50, as shown in FIG. 4. The actuator 50 comprises an upstand 52 that is operably linked to the push-button 4, such that the dose counter actuator 50 is displaced downwardly (as viewed in FIG. 4) when the push-button 4 is depressed, and is returned to its rest position when the push-button 4 is released.

The actuator 50 also has a portion that engages the end plate 42 of the collector spool 40 so as to effect rotation of the collector spool 40 on depression and release of the push-button 4, as discussed above. This portion comprises downwardly-extending first and second actuator arms 54, 56, each with an arcuate engagement member 55,57 at its lower end for engaging a peg 44 of the end plate 42. In particular, the engagement member 55 of the first actuator arm 54 is adapted to engage the upper surface of a peg 44, pushing that peg 44 downwards, and the engagement member 57 of the second actuator arm 56 is hooked, so as to engage the lower surface of a peg 44.

Figure 5:
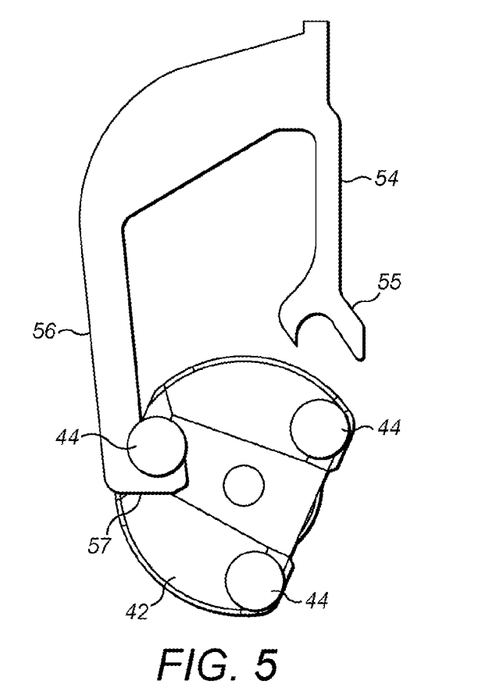
FIG. 5 is a view of part of the dose counter actuator in engagement with the collector spool, when the dose counter actuator is in the rest configuration.
Figure 6:
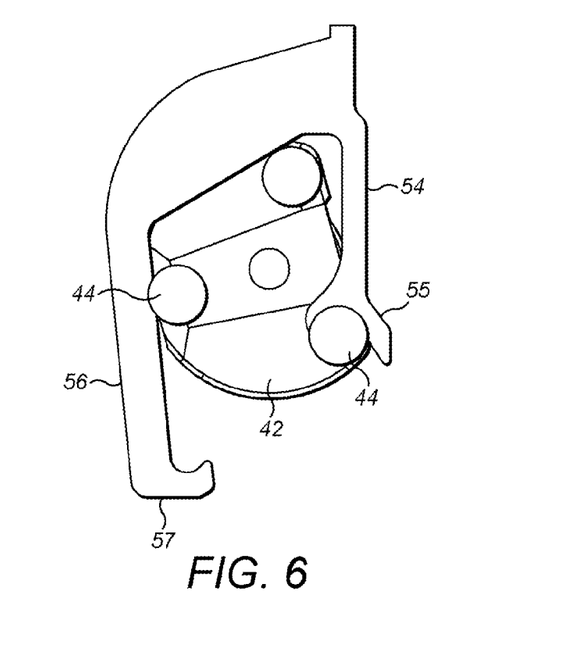
FIG. 6 is a view similar to that of FIG. 5, but when the dose counter actuator is in a depressed configuration.

The first and second actuator arms 54, 56 are shown in FIGS. 5 and 6 in engagement with the end plate 42 of the collector spool 40. Before depression of the push-button 4, and downward displacement of the dose counter actuator 50, the second actuator arms 56 engages a peg 44 of the end plate 42, as shown in FIG. 5. In particular, the engagement member 57 of the second actuator arm 56 is in engagement with the lower surface of a peg 44 on the left-hand side of the end plate 42 (as viewed in FIG. 5).

Depression of the push-button 4, and hence downward displacement of the dose counter actuator 50, causes the engagement member 55 of the first actuator arm 54 to engage the upper surface of the peg 44, and urge that peg 44 downwards. This causes the endplate 42, and hence the collector spool 40, to rotate in a clockwise direction. The engagement member 57 of the second actuator arm 56 will be displaced downwardly by this action (FIG. 6), freeing it from the peg 44 with which it was in contact.

Release of the push-button 4, and hence upward displacement of the actuator 50, will cause the engagement member of the second actuator arm 56 to return to its rest position, at which it engages a peg 44 from below, thereby holding the endplate 42, and hence the collector spool 40, in the position to which it has been rotated. The arrangement is then once again as shown in FIG. 5 (but with the engagement members of the second actuator arm 56 engaged with a different peg 44).

Operation of the actuator 50, by depression of the push-button 4, also of course causes a dose of medicament (or medicaments) to be dispensed. The manner in which this is achieved is specific to the dry powder inhaler of which the dose counter mechanism forms part, but may be as described in EP1233805B.

As described above, each depression and release of the push-button 4 will cause a dose of medicament to be dispensed, and the collector spool 40 to rotate 120° so that the next number in the series of numbers printed on the tape 20 is visible to the user.

As noted above, the dose counter mechanism incorporates a device locking mechanism. The manner in which this operates is illustrated in FIGS. 7 to 9.

Figure 7:
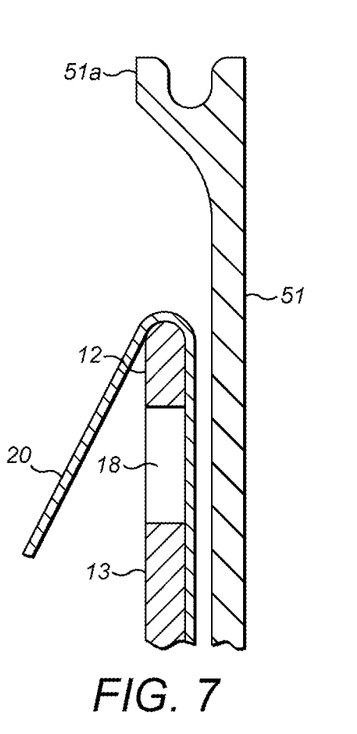
FIG. 7 is a sectional view illustrating the interaction of a locking arm that forms part of the dose counter actuator with the dose counter mechanism, when the dose counter actuator is in the rest configuration.

Referring first to FIG. 7, when the actuator 50 is depressed from, and then returns to, its rest configuration, the locking arm 51 reciprocates adjacent to the portion of the tape 20 that is supported by the rear wall 13 of the tape housing 10. The tip of the locking arm 51 is bifurcated, having a projection 51a that projects towards the tape 20.

Figure 8:
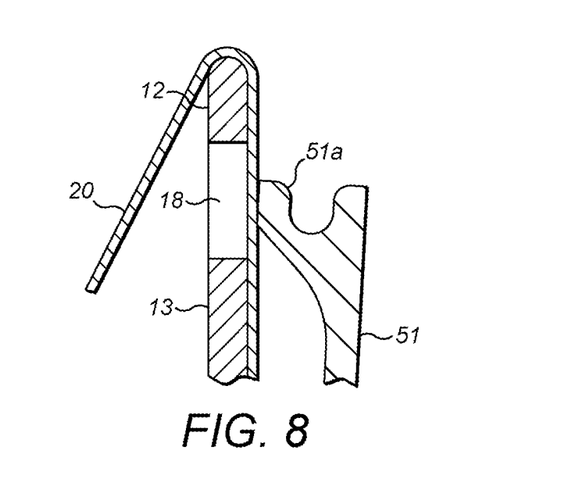
FIG. 8 is a view similar to FIG. 7, but with the dose counter actuator in the depressed configuration.

As shown in FIG. 8, in the downward stroke of the actuator 50, the projection 51a bears against the tape 20, with the result that the locking arm 51, which is somewhat resilient, is slightly deflected. At the lowest extent of its travel, the projection 51a is disposed adjacent to the opening 18 in the rear wall 13 of the tape housing 10. However, the tape 20 occludes the opening 18, so that the projection 51a rides over the tape 20 and the movement of the projection 51a is not interfered with by the opening 18.

Figure 9:
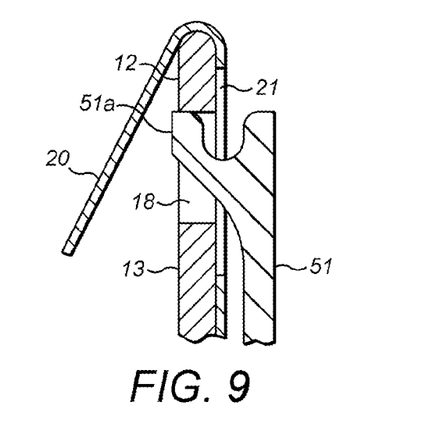
FIG. 9 is a view similar to FIGS. 7 and 8, but showing the dose counter actuator in a locked configuration, after dispensing of the final dose of medicament from the inhaler.
Figure 10:
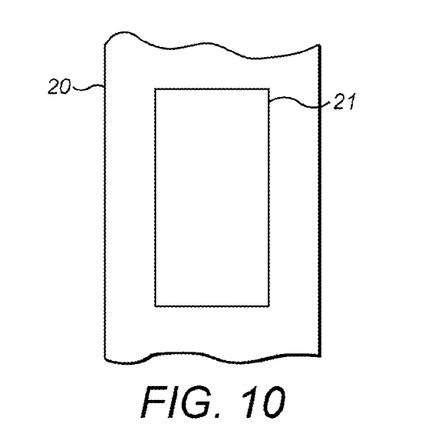
FIG. 10 shows the part of the tape with an opening that permits locking of the dose counter in the manner illustrated in FIGS. 7 to 9.

As shown in FIGS. 9 and 10, however, a slot 21 is formed in the tape 20. The slot 21 is positioned in the tape 20 such that the slot 21 comes into registration with the opening 18 when the last of the predetermined number of actuations of the inhaler 1 has occurred.

In the configuration depicted in FIG. 8, the slot 21 is positioned below the opening 18 (and so is not visible in FIG. 8). Further actuation of the device, however, brings the slot 21 to the position shown in FIG. 9, where the slot 21 is aligned with the opening 18. Instead of the locking arm 51 returning towards its rest configuration (FIG. 7) following that actuation, the resilience of the locking arm 51 causes the projection 51a to pass through the slot 21 and to engage the opening 18. The travel of the actuator 50 back to its rest configuration is thereby arrested, locking the actuator 50 in its depressed condition. Further operation of the device is thereby prevented and it is impossible for the user to continue to use the device.

Figure 11:
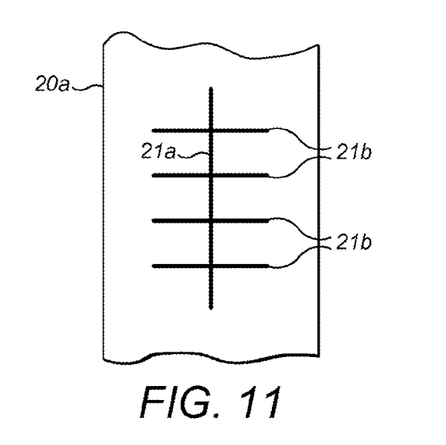
FIG. 11 shows an alternative form of tape with an arrangement of slits to permit locking of the dose counter.

Finally, FIG. 11 shows an alternative tape 20a. In this embodiment, the tape 20a is not formed with an opening, but with an arrangement of slits including an axial slit 21a that intersects with four shorter transverse slits 21b. The effect of these slits 21a, 21b is to permit the projection 51a to penetrate through the tape 20a when the slits 21a, 21b come into registration with the opening 18. The slits 21a, 21b thus function in the same manner as the opening 21 of the tape 20 of FIG. 10. However, this embodiment offers the advantage that no material is cut from the tape 20a during manufacture and no fragments of tape material are created that could potentially contaminate the device and/or be inhaled by a user of the device.

The invention claimed is:

1. A medicament delivery device comprising a push-button, a dispensing actuator for successively dispensing a predetermined number of unit doses of a medicament, a dose counter actuator and a locking mechanism for preventing further operation of the dispensing actuator after dispensing of said predetermined number of unit doses, characterised in that said locking mechanism comprises
   a resilient member,
   a recess or opening in a component of the device adjacent to the resilient member, with which the resilient member is engageable to disable operation of the dispensing actuator, and
   a barrier member that prevents engagement of the resilient member and the recess or opening until said predetermined number of unit doses has been dispensed,
   wherein operation of the device is brought about by means of the push-button which acts upon the dispensing actuator and the dose counter actuator that are integrally formed as a single component that undergoes a reciprocating action, and the push-button not only causes dispensing of a unit dose of medicament, but also operates a dose counting mechanism that provides to a user of the device an indication of the number of doses that have been dispensed or alternatively the number of doses that remain to be dispensed; wherein the resilient member is an elongate arm which is formed integrally with the dose counter actuator and which is displaced along an axis parallel to the axis of reciprocating movement of the dose counter actuator; and wherein the barrier member is part of the dose counting mechanism, the barrier member being interposed between the resilient member and the recess or opening until the last of the predetermined number of unit doses has been dispensed, wherein operation of the device to dispense the last of the predetermined doses has the effect of removing the barrier member from between the resilient member and the recess or opening, thereby permitting the resilient member to engage the recess or opening and preventing further operation of the device.

2. A medicament delivery device as claimed in claim 1, which is an inhaler.

3. A medicament delivery device as claimed in claim 2, which is a dry powder inhaler.

4. A medicament delivery device as claimed in claim 1, which comprises a reservoir in which a bulk quantity of medicament is held, the unit doses being dispensed as aliquots from that bulk quantity.

5. A medicament delivery device as claimed in claim 1, which dispenses unit doses of a single medicament.

6. A medicament delivery device as claimed in claim 1, which dispenses unit doses of a formulation containing two or more medicaments.

7. A medicament delivery device as claimed in claim 1, which dispenses unit doses of two or more medicaments from separate reservoirs within the device, those unit doses then being administered to the patient simultaneously.

8. A medicament delivery device as claimed in claim 1, wherein the arm has a projection that in the course of its reciprocating action is brought into registration with the recess or opening.

9. A medicament delivery device as claimed claim 1, wherein the dose counting mechanism has indicia showing the number of doses dispensed or remaining carried on an element that is displaced upon each actuation.

10. A medicament delivery device as claimed in claim 9, wherein the element comprises the barrier member.

11. A medicament delivery device as claimed in claim 1, in which the dose counting mechanism comprises a tape that carries indicia showing the number of doses dispensed or remaining, wherein the tape comprises the barrier member.

12. A medicament delivery device as claimed in claim 11, wherein the tape is wound on a take-up spool and is indexed upon each actuation of the device.

13. A medicament delivery device as claimed in claim 11, wherein the tape passes between the resilient member and the recess or opening during at least part of the actuation process, and thereby prevents engagement of the resilient member with the recess or opening.

14. A medicament delivery device as claimed in claim 11, wherein the tape has an opening that is brought into registration with the recess or opening upon dispensing of the last of the predetermined doses, thereby removing the barrier between the recess or opening and the resilient member and allowing the recess or opening and the resilient member to engage.

15. A medicament delivery device as claimed in claim 11, wherein the tape has one or more slits formed in it, such that the resilient member is able to penetrate the tape in the region of the slit(s).

16. A medicament delivery device as claimed in claim 15, wherein the tape is formed with an axial slit that is intersected by one or more transverse slits.

17. A medicament delivery device as claimed in claim 1, wherein the resilient member engages the recess or opening when the actuator is in its depressed position.

18. A medicament delivery device as claimed in claim 1, which is charged with one or more medicaments selected from the group consisting of β-agonists, non-selective beta-stimulants, xanthine bronchodilators, anticholinergics, mast cell stabilisers, bronchial anti-inflammatory agents, and steroids and/or salts or derivatives thereof.

19. A medicament delivery device as claimed in claim 1, which is charged with a combination of medicaments selected from the group consisting of (1) beclomethasone dipropionate and formoterol, (2) beclomethasone dipropionate and salmeterol, (3) fluticasone and formoterol, (4) fluticasone and salmeterol, (5) budesonide and formoterol, (6) budesonide and salmeterol, (7) flunisolide and formoterol, (8) flunisolide and salmeterol, (9) ciclesonide and salmeterol, (10) ciclesonide and formoterol, (11) mometasone and salmeterol and (12) mometasone and formoterol.

20. A medicament delivery device as claimed in claim 18, wherein the β-agonists are selected from the group consisting of fenoterol, formoterol, pirbuterol, reproterol, rimiterol, salbutamol, salmeterol and terbutaline and/or salts or derivatives thereof; wherein the non-selective beta-stimulant is isoprenaline and/or salts or derivatives thereof; wherein the xanthine bronchodilators are selected from the group consisting of theophylline, aminophylline and choline theophyllinate and/or salts or derivatives thereof; wherein the anticholinergics are selected from the group consisting of ipratropium bromide, oxitropium and tiotropium and/or salts or derivatives thereof; wherein the mast cell stabilisers are selected from the group consisting of sodium cromoglycate and ketotifen and/or salts or derivatives thereof; wherein the bronchial anti-inflammatory agent is nedocromil sodium and/or salts or derivatives thereof; and wherein the steroids are selected from the group consisting of beclomethasone, fluticasone, budesonide, flunisolide, triamcinolone, mometasone and ciclesonide and/or salts or derivatives thereof.

\* \* \* \* \*